(12) United States Patent
Dai et al.

(10) Patent No.: US 10,966,729 B1
(45) Date of Patent: Apr. 6, 2021

(54) PNEUMATIC PHYSIOTHERAPY APPARATUS WITH OPTIMIZED COMPRESSION

(71) Applicant: JKH Health Co., Ltd., Shenzhen (CN)

(72) Inventors: Quanqin Dai, Diamond Bar, CA (US); Pu Jiang, Shenzhen (CN); Baohua Jiang, Shenzhen (CN)

(73) Assignee: JKH Health Co., Ltd., Shenzhen (CN)

( * ) Notice: Subject to any disclaimer, the term of this patent is extended or adjusted under 35 U.S.C. 154(b) by 0 days.

(21) Appl. No.: 17/065,718

(22) Filed: Oct. 8, 2020

(30) Foreign Application Priority Data

Sep. 22, 2020 (CN) .......................... 202022095510.5

(51) Int. Cl.
*A61B 17/135* (2006.01)
*A61B 17/00* (2006.01)

(52) U.S. Cl.
CPC ............... *A61B 17/1355* (2013.01); *A61B 2017/00544* (2013.01)

(58) Field of Classification Search
CPC .............. A61B 5/02233; A61B 17/132; A61B 17/1322; A61B 17/135; A61B 17/1355; A61F 5/34
See application file for complete search history.

(56) References Cited

U.S. PATENT DOCUMENTS

| | | | |
|---|---|---|---|
| 5,496,262 A * | 3/1996 | Johnson, Jr. ......... | A61H 9/0078 601/152 |
| 2019/0021918 A1* | 1/2019 | Squitieri ............ | A61G 7/05769 |

* cited by examiner

*Primary Examiner* — Thomas McEvoy
(74) *Attorney, Agent, or Firm* — Karthik Murthy; Murthy Patent Law PLLC

(57) ABSTRACT

A pneumatic physiotherapy apparatus with optimized compression, including a wrap and a controller. The wrap includes an outer wrap and an inner airbag set; the controller can be fixedly connected to, detachably connected to, or separately connected to the outer wrap; the inner airbag set includes the first airbag and the second airbag that are interconnected and overlapped; the controller contains an inflating motor and an integrated control board that are electrically connected. The inflating motor that is controlled by the integrated control board inflates the second airbag first and then the first airbag to achieve the overlapped compression between the second airbag and the first airbag. Therefore, the user can use the pneumatic physiotherapy apparatus with optimized compression to promote blood flow, improve blood circulation, prevent deep vein thrombosis and other diseases, and improve user experience in the treatment areas.

7 Claims, 7 Drawing Sheets

PNEUMATIC PHYSIOTHERAPY APPARATUS WITH OPTIMIZED COMPRESSION

TECHNICAL FIELD

The invention relates to an pneumatic physiotherapy apparatus with optimized compression.

BACKGROUND

The pneumatic physiotherapy apparatus is used to repeatedly inflate and deflate the airbag wrapped on the extremities (such as limbs) from the distal to the proximal of the extremities to form sequential compression on the extremities and tissues, thereby promoting blood flow, improving blood circulation, and helping prevent or treat blood diseases. In order to achieve sequential compression from the distal to the proximal of the extremities, the prior art usually applies a divider (also called an isolation peninsula) in the middle area of an inflatable airbag to separate the first lower section and the second upper section of the airbag, and forms an air flow passageway between the first lower section and the second upper section. During the period of inflation, the air flow first enters the first lower section of the airbag, and then flows to the second upper section through the air flow passageway, so that both the first lower section and the second upper section of the airbag reach a preset pressure. However, the divider of the airbag cannot be inflated, resulting in little or no air pressure in that middle area of the airbag. In other words, the treatment area around the divider may not be able to reach the required pressure, and there are blind spots and shortcomings with insufficient pressure. Therefore, the whole treatment area may not be able to reach the full coverage of compression during use, which can affect the user experience and even the treatment effectiveness. Therefore, further improvements are necessary.

SUMMARY

The purpose of the invention is to provide a pneumatic physiotherapy apparatus with optimized compression to overcome the problems set forth above in the prior art.

A pneumatic physiotherapy apparatus with optimized compression designed for this purpose includes a wrap and a controller. The wrap includes an outer wrap and an inner airbag set; the controller is fixedly connected to, detachably connected to, or separately connected to the outer wrap; the inner airbag set includes the first airbag and the second airbag that are interconnected and overlapped; the controller contains an inflation motor and an integrated control board that are electrically powered by a single battery or multiple batteries inside the controller or by a battery bank/AC adapter outside the controller. The inflation motor that is controlled by the integrated control board inflates the second airbag first and then inflates the first airbag to achieve the overlapped compression between the second airbag and the first airbag.

The size of the first airbag is bigger than that of the second airbag, and the second airbag is located inside the lower section of the first airbag. There is an inflation nozzle on the second airbag, which also contains one or more air flow passageways inside the first airbag. Through the air flow passageways, the air flow enters the first airbag from the second airbag.

There are a first connection tubing and an inflation tubing between the inflation nozzle and the inflation motor. One end of the inflation nozzle is connected to the inflation motor through the first connection tubing and the inflation tubing; the other end of the inflation nozzle is connected to the second airbag through the first airbag. The inflation motor controlled by the integrated control board generates air flow; the air flow from the inflation motor enters the second airbag through the first connection tubing, inflation tubing and the inflation nozzle. When the air pressure in the second airbag rises to a certain level, the air flow starts to enter the first airbag from the second airbag through the air flow passageway.

The controller also contains a solenoid valve and a pressure detection valve; the solenoid valve, pressure detection valve, and the inflation motor are electrically connected to the integrated control board. The first airbag includes a pressure detection and deflation nozzle. There are a second connection tubing and a deflation tubing between the pressure detection and deflation nozzle and the pressure detection valve; the pressure detection and deflation nozzle is connected to the pressure detection valve and the solenoid valve via the second connection tubing and deflation tubing. When the inflation pressure inside the first airbag and the second airbag reaches a preset value, the pressure detection valve detects and sends signals to the integrated control board. After receiving signals, the integrated control board will stop the inflation motor. After the inflation motor stops, the first airbag and the second airbag will maintain a preset pressure for a certain period of time prior to deflation, or immediately deflate through the pressure detection and deflation nozzle, the deflation tubing, the second connection tubing, and the solenoid valve in sequence.

A single or multiple control button is provided on the front or side of the controller; the control button can be a convex button, a concave button, a flat button, or a touch button. A display indication is arranged on the front or side of the controller; the indication can be a digital display, an LCD display screen, or a light indicator.

The wrap can be used to cover different treatment areas, including leg, arm, buttock, waist, or a combination of the above.

The connection between the controller and the wrap can be integrally fixed, attached/detached, or separated via tubing.

A connecting bracket is fixedly arranged inside the outer wrap. The connecting bracket contains several screw posts and/or buckle grooves, and is fixedly connected to the controller through the screw posts and/or buckle grooves to form an integrally fixed connection between the controller and the wrap.

In an alternative embodiment, a connecting bracket is fixedly arranged on the outer wrap. The connecting bracket contains a number of sliding grooves, snapping grooves, magnetic buckles, or concealed buckles; and the connecting bracket is detachably connected to the controller through the sliding grooves, snapping grooves, magnetic buckles, or concealed buckles, to form a detachable connection between the controller and the wrap.

In another alternative-embodiment, an external air tubing is provided between the controller and the wrap, and the external air tubing is used to form a separate connection between the controller and the wrap.

The controller optionally contains a USB interface on its front or side for transferring usage data, a pluggable memory card on its front or side for recording the usage data, or a Bluetooth module inside for transferring the usage data.

Through the above-mentioned improvements, the invention is provided with a first airbag and a second airbag that are overlapped and interconnected. The size of the first airbag is larger than that of the second airbag, and the second airbag is located inside the lower section of the first airbag. When working, the inflation motor controlled by the integrated control board first inflates the second airbag, and then enters the first airbag from the second airbag. This method of inflation achieves an overlapped compression between the first airbag and the second airbag, and effectively avoids blind spots and shortcomings in the prior art. Therefore, users can use the pneumatic physiotherapy apparatus of this invention to promote blood flow, improve blood circulation, prevent deep vein thrombosis and other diseases, and improve user experience in the treatment areas (such as limbs).

In general, this invention has the characteristics of simple and reasonable structure, excellent performance, convenient use, safety, reliability, comfort, and strong practicability.

DETAILED DESCRIPTION

The present invention will be further described below with reference to the drawings and embodiments.

The First Embodiment

Referring to FIGS. 1 to 5, the pneumatic physiotherapy apparatus with optimized compression includes a wrap and a controller 1. The wrap includes an outer wrap 2 and an inner airbag set 3; the controller 1 is fixedly connected to (or integrally fixed on) the outer wrap 2; the inner airbag set 3 contains a first airbag 5 and a second airbag 6 that are overlapped and interconnected; the controller 1 contains an inflation motor 7 and an integrated control board 22 that are electrically powered by a single battery or multiple batteries inside the controller 1 or by a battery bank/AC adapter outside the controller 1. The inflation motor 7 that is controlled by the integrated control board 22 inflates the second airbag 6 first, and then inflates the first airbag 5 to realize the overlapped compression between the second airbag 6 and the first airbag 5.

Figure 1:
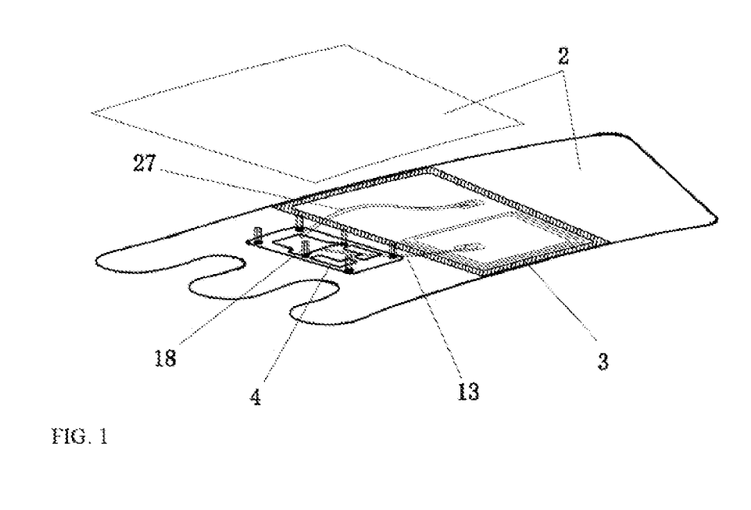
FIG. 1 is a schematic diagram of the exploded structure of the first embodiment of the present invention.
Figure 2:
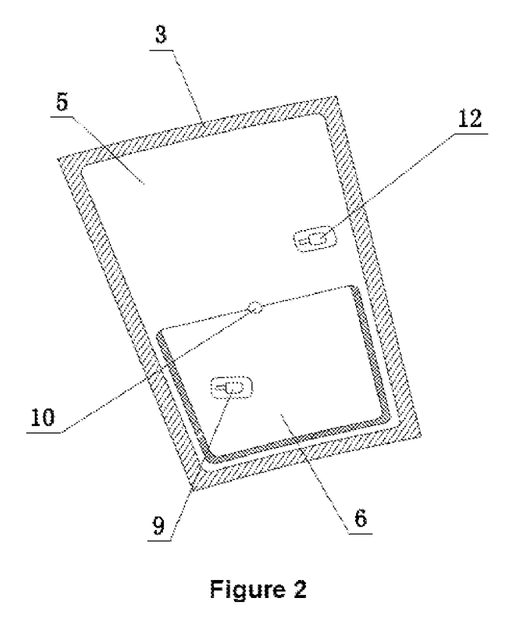
FIG. 2 is a schematic diagram of the inner airbag set of the first embodiment of the present invention.

Specifically, the size of the first airbag 5 is larger than that of the second airbag 6, and the second airbag 6 is located inside the lower section of the first airbag 5. There is an inflation nozzle 9 on the second airbag 6, which also contains one or more air flow passageways 10 inside the first airbag 5. Through the air flow passageway 10, the air flow enters from the second airbag 6 to the first airbag 5.

Figure 4:
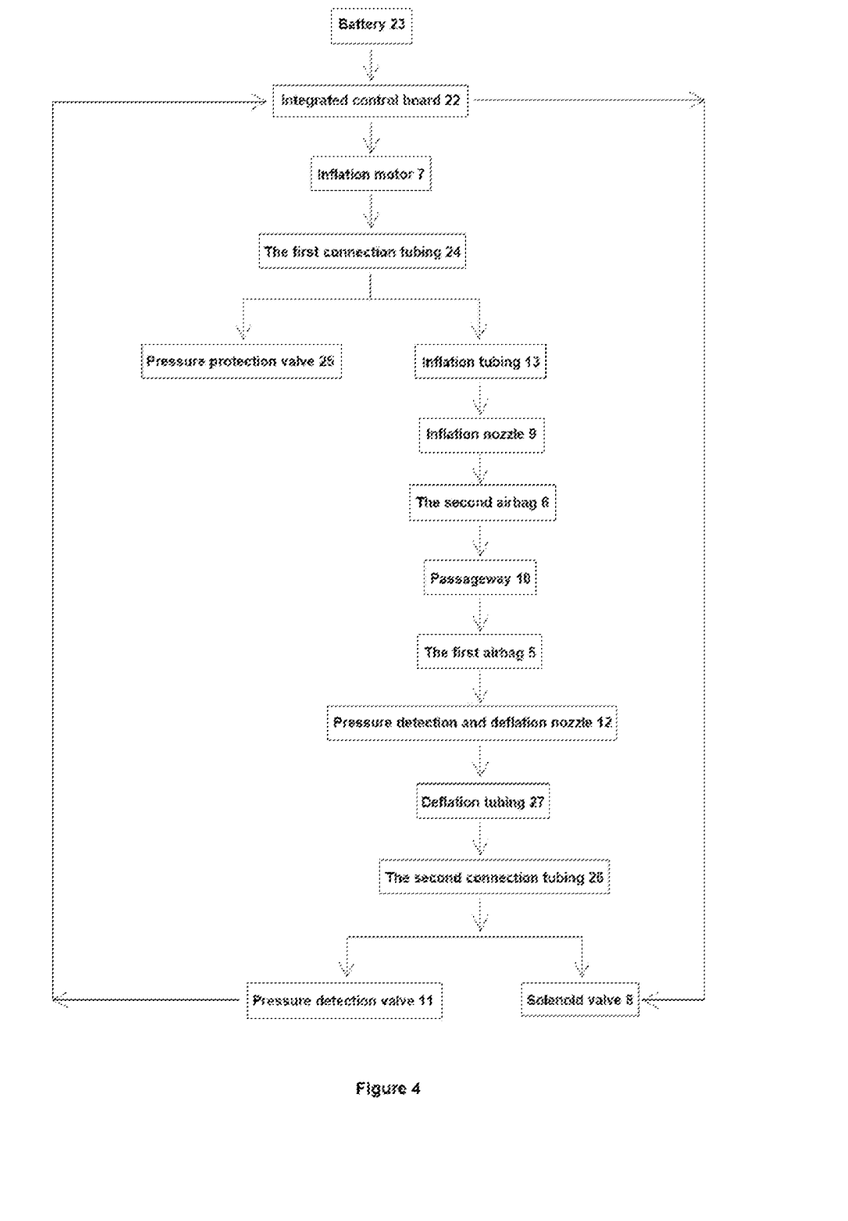
FIG. 4 is a schematic diagram of the working principle of the first embodiment of the present invention.

There are a first connection tubing 24 and an inflation tubing 13 between the inflation nozzle 9 and the inflation motor 7. One end of the inflation nozzle 9 is connected to the inflation motor 7 through the first connection tubing 24 and the inflation tubing 13; the other end of the inflation nozzle 9 is connected to the second airbag 6 through the first airbag 5.

The inflation motor 7 controlled by the integrated control board 22 generates air flow. The air flow from the inflation motor 7 enters the second airbag 6 through the first connection tubing 24, inflation tubing 13 and the inflation nozzle 9. When the air pressure in the second airbag 6 rises to a certain level, the air flow starts to enter the first airbag 5 from the second airbag 6 through the air flow passageway 10.

Figure 3:
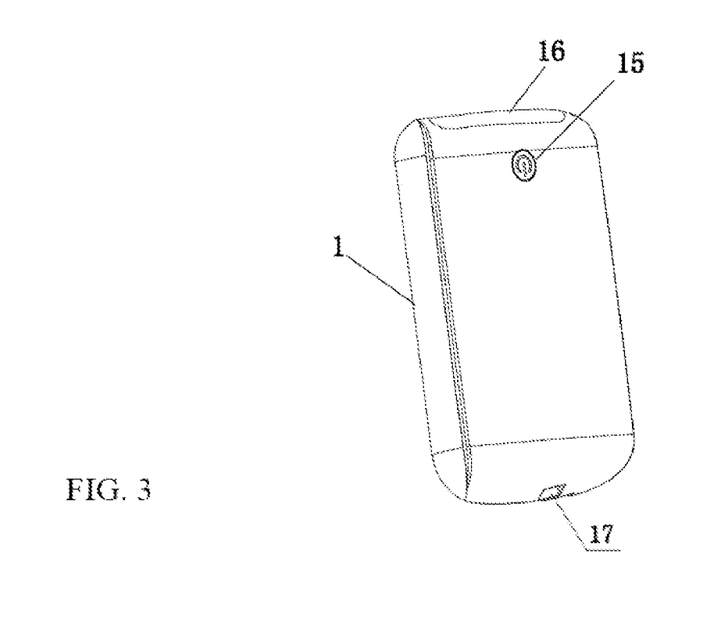
FIG. 3 is a schematic diagram of the controller of the first embodiment of the present invention.

In order to detect and control the air pressure inside the first airbag 5 and the second airbag 6, the controller 1 also contains a solenoid valve 8 and a pressure detection valve 11. The solenoid valve 8, pressure detection valve 11, and the inflation motor 7 are electrically connected to the integrated control board 22. The first airbag includes a pressure detection and deflation nozzle 12. The pressure detection and deflation nozzle 12 not only can release the pressure from the first airbag 5 and the second airbag 6, but also control the pressure of the first airbag 5 and the second airbag 6 via the pressure detection valve 11.

There are a second connection tubing 26 and a deflation tubing 27 between the pressure detection and deflation nozzle 12 and the pressure detection valve 11. The pressure detection and deflation nozzle 12 is connected to the pressure detection nozzle 11 and the solenoid valve 8 via the second connection tubing 26 and the deflation tubing 27. When the inflation pressure inside the first airbag 5 and the second airbag 6 reaches the preset value, the pressure detection valve 11 detects and sends signals to the integrated control board 22. After receiving signals, the integrated control board 22 will stop the inflation motor 7. After the inflation motor 7 stops, the first airbag 5 and the second airbag 6 will maintain the preset pressure for a certain period of time prior to deflation, or immediately deflate through the pressure detection and deflation nozzle 12, the deflation tubing 27, the second connection tubing 26, and the solenoid valve 8 in sequence.

In order to avoid the safety concern caused from the excessive pressure in the first airbag 5 and the second airbag 6, a pressure protection valve 25 is equipped in the controller 1. The pressure protection valve 25 is connected to the first connection tubing 24. When the pressure inside the first airbag 5 and the second airbag 6 is excessive and beyond an allowable pressure range, the pressure protection valve 25 will be activated, and the excessive pressure will release from the first airbag 5 and the second airbag 6.

During operation, the inflation motor 7 is connected to the pressure protection valve 25 and the inflation tubing 13 through the first connection tubing 24. The other end of the inflation tubing 13 is connected to the inflation nozzle 9. The inflation motor 7 controlled by the integrated control board 22 first inflates the second airbag 6, and then enters the first airbag 5 from the second airbag 6 through the air flow passageway 10. This method of inflation achieves an overlapped compression between the first airbag 5 and the second airbag 6, and effectively avoids blind spots and shortcomings in the prior art. Therefore, users can use the pneumatic physiotherapy apparatus of this invention to promote blood flow, improve blood circulation, prevent deep vein thrombosis and other diseases, and improve user experience in the treatment areas (such as limbs).

The controller 1 also includes a first housing 19 and a second housing 20; the first housing 19 and the second housing 20 are fixedly connected to each other, and form a cavity 21 between the two housings. The cavity 21 covers the inflation motor 7, the solenoid valve 8, the pressure detection valve 11, the first connection tubing 24, the pressure protection valve 25, the integrated control board 22, the battery 23, and the second connection tubing 26.

For ease of use, a single or multiple control button 15 is on the front or side of the controller 1. The control button 15 can be shaped in many different ways, such as a convex button, a concave button, a flat button, or a touch button. The user can use the control button 15 to operate the pneumatic physiotherapy apparatus with optimized compression.

A display indication 16 is arranged on the front or side of the controller 1. The display indication 16 can be a digital display, an LCD display screen, or a light indicator. The user can observe the working state of the controller 1 through the display indication 16 when in use.

The inflation tubing 13 and the deflation tubing 27 in this first embodiment are inside the wrap. The wrap can be used to cover different treatment areas, including the leg, arm, buttock, waist, or a combination of the above. The wrap in this first embodiment is for any limb, and is used as an example for description. In use, a user wears the wrap on the limb, and operates the controller 1 to achieve an overlapped compression between the first airbag 5 and the second airbag 6. Therefore, this invention of a pneumatic physiotherapy apparatus with optimized compression can promote blood flow, improve blood circulation, and help prevent deep vein thrombosis and other diseases.

Figure 5:
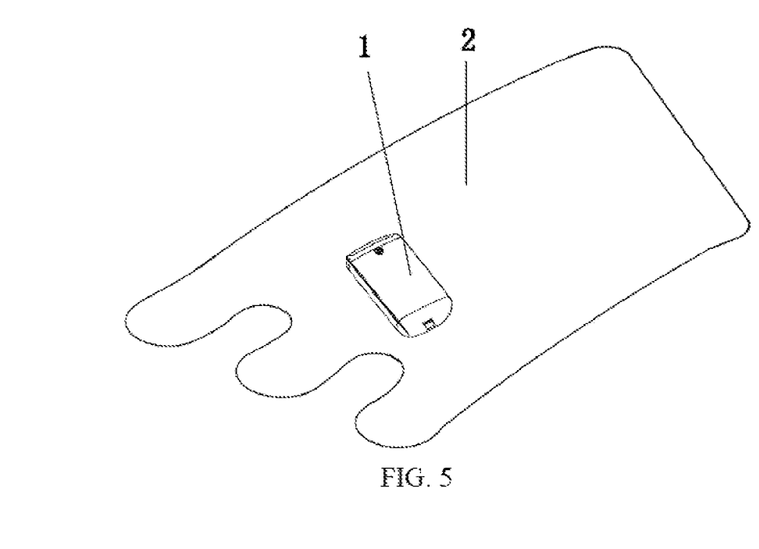
FIG. 5 is a schematic diagram of the integrally fixed structure of the wrap and the controller of the first embodiment of the present invention.

In this first embodiment, the connection between the controller 1 and the wrap is fixedly connected (or integrally fixed) to each other. Specifically, a connecting bracket 4 is fixedly arranged inside the outer wrap 2. The connecting bracket 4 contains several screw posts and/or buckle grooves 18, and is fixedly connected to the controller 1 through the screw posts and/or buckle grooves 18 to form an integrally fixed connection between the controller 1 and the wrap.

In order for the user to view the usage data of the pneumatic physiotherapy apparatus with optimized compression, the front or side of the controller 1 is optionally provided with a USB interface 17. The controller 1 can connect to the data cable and the computer through the USB interface 17 to read the usage data.

In an alternative embodiment, a memory card can be optionally provided on the front or side of the controller 1. When the memory card is plugged into the front or side of the controller 1, the memory card can record the usage data of the pneumatic physiotherapy apparatus with optimized compression for the user to read.

In another alternative embodiment, the controller 1 is optionally equipped with a Bluetooth module, and the user can wirelessly connect a smart device (such as a smart phone) to the Bluetooth module to read the usage data of the pneumatic physiotherapy apparatus with optimized compression.

The Second Embodiment

In this second embodiment, the controller 1 and the wrap are connected detachably, and the controller 1 can be attached to and detached from the wrap.

Figure 6:
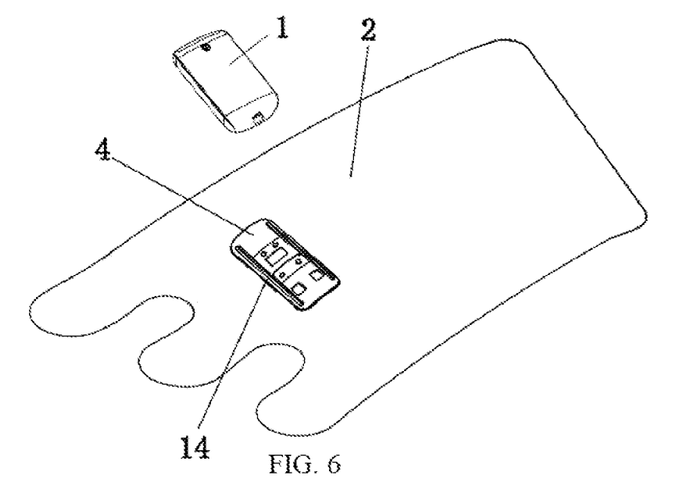
FIG. 6 is a schematic diagram of the detachable structure of the wrap and the controller of the second embodiment of the present invention.

Referring to FIG. 6, the difference between this second embodiment and the first embodiment is that the controller 1 is detachably connected to the outer wrap 2 in this second embodiment. Therefore, the same controller 1 can be detachably used on the wrap of different types.

Specifically, the controller 1 and the wrap are detachably connected. The connecting bracket 4 is fastened on the wrap and contains a plurality of sliding grooves 14, snapping grooves, magnetic buckles, or concealed buckles. The connecting bracket 4 is detachably connected to the controller 1 through the sliding grooves 14, snapping grooves, magnetic buckles, or concealed buckle to form a detachable connection between the controller 1 and the wrap.

Other undescribed parts in this second embodiment are the same as in the first embodiment.

The Third Embodiment

In this third embodiment, an external tubing is located between the controller 1 and the wrap, and the external tubing is used to form a separate connection between the controller 1 and the wrap.

Figure 7:
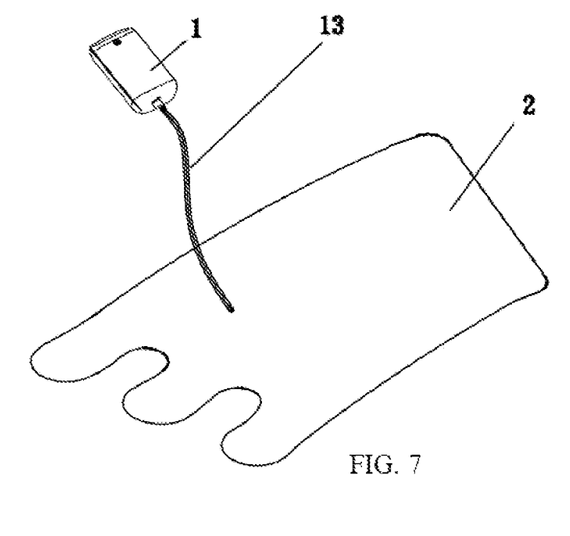
FIG. 7 is a schematic diagram of the separated structure of the wrap and the controller of the third embodiment of the present invention.

Referring to FIG. 7, the difference between this third embodiment and the first embodiment is the controller 1 and the wrap are separately connected via an external tubing.

Specifically, the inflation tubing 13 is outside the wrap. One end of the inflation tubing 13 is connected to the inflation motor 7 of the controller 1, and the other end is connected to the inflation nozzle 9 inside the wrap. The controller 1 and the wrap are connected to each other through the inflation tubing 13 outside the wrap to form a separate connection between the controller 1 and the wrap.

Other undescribed parts in this third embodiment are the same as in the first embodiment.

In another embodiment, a pneumatic physiotherapy apparatus with optimized compression comprising a wrap and a controller:
  wherein the wrap includes an outer wrap and an inner airbag set;
  wherein the controller is fixedly connected to the outer wrap;
  wherein the inner airbag set includes the first airbag and the second airbag that are interconnected and overlapped;
  wherein the controller contains an inflation motor and an integrated control board; wherein the inflation motor is controlled by the integrated control board;
  wherein the inflation motor inflates the second airbag first and then the first airbag to achieve overlapped compression between the second airbag and the first airbag;
  wherein a connecting bracket is fixedly arranged inside the outer wrap;
  wherein the connecting bracket contains several screw posts and/or buckle grooves, and is fixedly connected to the controller through the screw posts and/or buckle grooves to form an integrally fixed connection between the controller and the wrap.

In another embodiment, a pneumatic physiotherapy apparatus with optimized compression comprising a wrap and a controller:
  wherein the wrap includes an outer wrap and an inner airbag set;
  wherein the controller is fixedly connected to the outer wrap;
  wherein the inner airbag set includes the first airbag and the second airbag that are interconnected and overlapped;
  wherein the controller contains an inflation motor and an integrated control board;

wherein the inflation motor is controlled by the integrated control board;
wherein the inflation motor inflates the second airbag first and then the first airbag to achieve overlapped compression between the second airbag and the first airbag;
wherein a connecting bracket is fixedly arranged inside the outer wrap;
wherein the connecting bracket contains several screw posts and/or buckle grooves, and is fixedly connected to the controller through the screw posts and/or buckle grooves to form an integrally fixed connection between the controller and the wrap;
wherein the controller contains a USB interface on its front or side for transferring the usage data, a pluggable memory card on its front or side for recording the usage data, or a Bluetooth module inside for transferring the usage data.

In another embodiment, a pneumatic physiotherapy apparatus with optimized compression comprising a wrap and a controller:
wherein the wrap includes an outer wrap and an inner airbag set;
wherein the controller is detachably connected to the outer wrap;
wherein the inner airbag set includes the first airbag and the second airbag that are interconnected and overlapped;
wherein the controller contains an inflation motor and an integrated control board; wherein the inflation motor is controlled by the integrated control board;
wherein the inflation motor inflates the second airbag first and then the first airbag to achieve overlapped compression between the second airbag and the first airbag;
wherein a connecting bracket is fixedly arranged on the outer wrap;
wherein the connecting bracket contains a number of sliding grooves, snapping grooves, magnetic buckles, or concealed buckles;
and wherein the connecting bracket is detachably connected to the controller through the sliding grooves, snapping grooves, magnetic buckles, or concealed buckles, to form a detachable connection between the controller and the wrap.

In another embodiment, a pneumatic physiotherapy apparatus with optimized compression comprising a wrap and a controller:
wherein the wrap includes an outer wrap and an inner airbag set;
wherein the controller is detachably connected to the outer wrap;
wherein the inner airbag set includes the first airbag and the second airbag that are interconnected and overlapped;
wherein the controller contains an inflation motor and an integrated control board; wherein the inflation motor is controlled by the integrated control board;
wherein the inflation motor inflates the second airbag first and then the first airbag to achieve overlapped compression between the second airbag and the first airbag;
wherein a connecting bracket is fixedly arranged on the outer wrap;
wherein the connecting bracket contains a number of sliding grooves, snapping grooves, magnetic buckles, or concealed buckles;
and wherein the connecting bracket is detachably connected to the controller through the sliding grooves, snapping grooves, magnetic buckles, or concealed buckles, to form a detachable connection between the controller and the wrap;
wherein the controller contains a USB interface on its front or side for transferring the usage data, a pluggable memory card on its front or side for recording the usage data, or a Bluetooth module inside for transferring the usage data.

In another embodiment, a pneumatic physiotherapy apparatus with optimized compression comprising a wrap and a controller:
wherein the wrap includes an outer wrap and an inner airbag set;
wherein the controller is separately connected to the outer wrap;
wherein the inner airbag set includes the first airbag and the second airbag that are interconnected and overlapped;
wherein the controller contains an inflation motor and an integrated control board; wherein the inflation motor is controlled by the integrated control board;
wherein the inflation motor inflates the second airbag first and then the first airbag to achieve overlapped compression between the second airbag and the first airbag;
wherein an external air tubing is provided between the controller and the wrap, and the external air tubing is used to form a separate connection between the controller and the wrap.

In another embodiment, a pneumatic physiotherapy apparatus with optimized compression comprising a wrap and a controller:
wherein the wrap includes an outer wrap and an inner airbag set;
wherein the controller is separately connected to the outer wrap;
wherein the inner airbag set includes the first airbag and the second airbag that are interconnected and overlapped;
wherein the controller contains an inflation motor and an integrated control board; wherein the inflation motor is controlled by the integrated control board;
wherein the inflation motor inflates the second airbag first and then the first airbag to achieve overlapped compression between the second airbag and the first airbag;
wherein an external air tubing is provided between the controller and the wrap, and the external air tubing is used to form a separate connection between the controller and the wrap;
wherein the controller contains a USB interface on its front or side for transferring the usage data, a pluggable memory card on its front or side for recording the usage data, or a Bluetooth module inside for transferring the usage data.

In another embodiment, a pneumatic physiotherapy apparatus with optimized compression comprising a wrap and a controller:
wherein the wrap includes an outer wrap and an inner airbag set;
wherein the controller is fixedly connected to, detachably connected to, or separately connected to the outer wrap;
wherein the inner airbag set includes the first airbag and the second airbag that are interconnected and overlapped;
wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be integrally fixed, attached/detached, or separated via tubing.

In another embodiment, a pneumatic physiotherapy apparatus with optimized compression comprising a wrap and a controller:

wherein the wrap includes an outer wrap and an inner airbag set;

wherein the controller is fixedly connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be integrally fixed; wherein a connecting bracket is fixedly arranged inside the outer wrap;

wherein the connecting bracket contains several screw posts and/or buckle grooves, and is fixedly connected to the controller through the screw posts and/or buckle grooves to form an integrally fixed connection between the controller and the wrap.

In another embodiment, a pneumatic physiotherapy apparatus with optimized compression comprising a wrap and a controller:

wherein the wrap includes an outer wrap and an inner airbag set;

wherein the controller is fixedly connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be integrally fixed; wherein a connecting bracket is fixedly arranged inside the outer wrap;

wherein the connecting bracket contains several screw posts and/or buckle grooves, and is fixedly connected to the controller through the screw posts and/or buckle grooves to form an integrally fixed connection between the controller and the wrap;

wherein the controller contains a USB interface on its front or side for transferring the usage data, a pluggable memory card on its front or side for recording the usage data, or a Bluetooth module inside for transferring the usage data.

In another embodiment, a pneumatic physiotherapy apparatus with optimized compression comprising a wrap and a controller:

wherein the wrap includes an outer wrap and an inner airbag set;

wherein the controller is detachably connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be attached/detached; wherein a connecting bracket is fixedly arranged on the outer wrap;

wherein the connecting bracket contains a number of sliding grooves, snapping grooves, magnetic buckles, or concealed buckles;

and wherein the connecting bracket is detachably connected to the controller through the sliding grooves, snapping grooves, magnetic buckles, or concealed buckles, to form a detachable connection between the controller and the wrap.

In another embodiment, a pneumatic physiotherapy apparatus with optimized compression comprising a wrap and a controller:

wherein the wrap includes an outer wrap and an inner airbag set;

wherein the controller is detachably connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be attached/detached; wherein a connecting bracket is fixedly arranged on the outer wrap;

wherein the connecting bracket contains a number of sliding grooves, snapping grooves, magnetic buckles, or concealed buckles;

wherein the connecting bracket is detachably connected to the controller through the sliding grooves, snapping grooves, magnetic buckles, or concealed buckles, to form a detachable connection between the controller and the wrap;

wherein the controller contains a USB interface on its front or side for transferring the usage data, a pluggable memory card on its front or side for recording the usage data, or a Bluetooth module inside for transferring the usage data.

In another embodiment, a pneumatic physiotherapy apparatus with optimized compression comprising a wrap and a controller:

wherein the wrap includes an outer wrap and an inner airbag set;

wherein the controller is separately connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be separated via tubing; wherein an external air tubing is provided between the controller and the wrap, and the external air tubing is used to form a separate connection between the controller and the wrap.

In another embodiment, a pneumatic physiotherapy apparatus with optimized compression comprising a wrap and a controller:

wherein the wrap includes an outer wrap and an inner airbag set;

wherein the controller is separately connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be separated via tubing; wherein an external air tubing is provided between the controller and the wrap, and the external air tubing is used to form a separate connection between the controller and the wrap;

wherein the controller contains a USB interface on its front or side for transferring the usage data, a pluggable memory card on its front or side for recording the usage data, or a Bluetooth module inside for transferring the usage data.

In another embodiment, a pneumatic physiotherapy apparatus with optimized compression comprising a wrap and a controller:

wherein the wrap includes an outer wrap and an inner airbag set;

wherein the controller is fixedly connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be integrally fixed.

In another embodiment, a pneumatic physiotherapy apparatus with optimized compression comprising a wrap and a controller:

wherein the wrap includes an outer wrap and an inner airbag set;

wherein the controller is detachably connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be detachably fixed.

In another embodiment, a pneumatic physiotherapy apparatus with optimized compression comprising a wrap and a controller:

wherein the wrap includes an outer wrap and an inner airbag set;

wherein the controller is separately connected to the outer wrap;

wherein the inner airbag set includes the first airbag and the second airbag that are interconnected and overlapped;

wherein the controller contains an inflation motor and an integrated control board; wherein the inflation motor is controlled by the integrated control board;

wherein the inflation motor inflates the second airbag first and then the first airbag to achieve overlapped compression between the second airbag and the first airbag;

wherein the connection between the controller and the wrap can be separated via tubing.

The above are the preferred solutions of the invention, showing and describing the basic principles, main features and advantages of the invention. Those skilled in the art should understand that the present invention is not limited by the above-mentioned embodiments. The above-mentioned embodiments and description only illustrate the principle of the present invention. There will be various changes and improvements; these changes and improvements fall within the scope of the claimed invention, which is defined by the appended claims and their equivalents.

The invention claimed is:

1. A pneumatic physiotherapy apparatus with optimized compression comprising a wrap and a controller:

wherein the wrap includes an outer wrap and an inner airbag set; wherein the controller is fixedly connected to, detachably connected to, or separately connected to the outer wrap; wherein the inner airbag set includes a first airbag and a second airbag that are interconnected and overlapped; wherein the controller contains an inflation motor and an integrated control board; wherein the inflation motor is controlled by the integrated control board; wherein the inflation motor inflates the second airbag first and then the first airbag to achieve overlapped compression between the second airbag and the first airbag, wherein the size of the first airbag is bigger than that of the second airbag, and the second airbag is located inside a lower section of the first airbag; wherein there is an inflation nozzle on the second airbag, the second airbag also containing one or more air flow Passageways inside the first airbag; wherein through the one or more air flow passageways, the air flow enters the first airbag from the second airbag, wherein there are a first connection tubing and an inflation tubing between the inflation nozzle and the inflation motor; wherein one end of the inflation nozzle is connected to the inflation motor through the first connection tubing and the inflation tubing; wherein the other end of the inflation nozzle is connected to the second airbag through the first airbag; wherein the inflation motor generates air flow wherein the air flow from the inflation motor enters the second airbag through the first connection tubing, inflation tubing and the inflation nozzle; wherein when the air pressure in the second airbag rises to a certain level, the air flow starts to enter the first airbag from the second airbag through the air flow passageway, wherein the controller contains a solenoid valve and a pressure detection valve: wherein the solenoid valve, the pressure detection valve, and the inflation motor are electrically connected to the integrated control board; wherein the first airbag includes a pressure detection and deflation nozzle; wherein there are a second connection tubing and a deflation tubing between the pressure detection and deflation nozzle and the pressure detection valve; wherein the pressure detection and deflation nozzle is connected to the pressure detection valve and the solenoid valve via the second connection tubing and the deflation tubing; wherein when the inflation pressure inside the first airbag and the second airbag reaches a preset value, the pressure detection valve detects and sends signals to the integrated control board; wherein after receiving signals, the integrated control board stops the inflation motor; wherein after the inflation motor stops, the first airbag and the second airbag maintain the inflation pressure at the preset value for a certain period of time prior to deflation, or immediately deflate through the pressure detection and deflation nozzle, the deflation tubing, the second connection tubing, and the solenoid valve in sequence.

2. The system of claim 1, further comprising
a single or multiple control button on the front or side of the controller;
wherein the control button can be a convex button, a concave button, a flat button, or a touch button.

3. The system of claim 1, further comprising:
a display indication is arranged on the front or side of the controller;
wherein the display indication can be a digital display, an LCD display screen, or a light indicator.

4. The system of claim 1, further comprising:
wherein the wrap can be used to cover different treatment areas, including leg, arm, buttock, waist, or a combination of the above.

5. The system of claim 1, further comprising:
when the controller is fixedly connected to the outer wrap, then:
  wherein a connecting bracket is fixedly arranged inside the outer wrap;
  wherein the connecting bracket contains several screw posts and/or buckle grooves, and is fixedly connected to the controller through the screw posts and/or buckle grooves to form an integrally fixed connection between the controller and the wrap;
when the controller is detachably connected to the outer wrap, then:
  wherein a connecting bracket is fixedly arranged on the outer wrap;
  wherein the connecting bracket contains a number of sliding grooves, snapping grooves, magnetic buckles, or concealed buckles;
  and wherein the connecting bracket is detachably connected to the controller through the sliding grooves, snapping grooves, magnetic buckles, or concealed buckles, to form a detachable connection between the controller and the wrap;
when the controller is separately connected to the outer wrap, then:
  wherein an external air tubing is provided between the controller and the wrap, and the external air tubing is used to form a separate connection between the controller and the wrap.

6. The system of claim 5, further comprising:
wherein the controller contains a USB interface on its front or side for transferring the usage data, a pluggable memory card on its front or side for recording the usage data, or a Bluetooth module inside for transferring the usage data.

7. A pneumatic physiotherapy apparatus with optimized compression comprising a wrap and a controller:
wherein the wrap includes an outer wrap and an inner airbag set;
wherein the controller is fixedly connected to, detachably connected to, or separately connected to the outer wrap;
wherein the inner airbag set includes the first airbag and the second airbag that are interconnected and overlapped;
wherein the controller contains an inflation motor and an integrated control board;
wherein the inflation motor is controlled by the integrated control board;
wherein the inflation motor inflates the second airbag first and then the first airbag to achieve overlapped compression between the second airbag and the first airbag;
wherein the size of the first airbag is bigger than that of the second airbag, and the second airbag is located inside a lower section of the first airbag;
wherein there is an inflation nozzle on the second airbag, the second airbag also containing one or more air flow passageways inside the first airbag;
wherein through the one or more airflow passageways, the air flow enters the first airbag from the second airbag;
wherein there are a first connection tubing and an inflation tubing between the inflation nozzle and the inflation motor;
wherein one end of the inflation nozzle is connected to the inflation motor through the first connection tubing and the inflation tubing;
wherein the other end of the inflation nozzle is connected to the second airbag through the first airbag;
wherein the inflation motor generates air flow;
wherein the air flow from the inflation motor enters the second airbag through the first connection tubing, inflation tubing and the inflation nozzle;
wherein when the air pressure in the second airbag rises to a certain level, the air flow starts to enter the first airbag from the second airbag through the air flow passageway;
wherein the controller contains a solenoid valve and a pressure detection valve;
wherein the solenoid valve, pressure detection valve, and the inflation motor are electrically connected to the integrated control board;
wherein the first airbag includes a pressure detection and deflation nozzle;
wherein there are a second connection tubing and a deflation tubing between the pressure detection and deflation nozzle and the pressure detection valve;
wherein the pressure detection and deflation nozzle is connected to the pressure detection valve and the solenoid valve via the second connection tubing and a deflation tubing;

wherein when the inflation pressure inside the first airbag and the second airbag reaches a preset value, the pressure detection valve detects and sends signals to the integrated control board;

wherein after receiving signals, the integrated control board stops the inflation motor;

wherein after the inflation motor stops, the first airbag and the second airbag maintain the inflation pressure at the preset value for a certain period of time prior to deflation, or immediately deflate through the pressure detection and deflation nozzle, the deflation tubing, the second connection tubing, and the solenoid valve in sequence;

wherein the wrap can be used to cover different treatment areas, including leg, arm, buttock, waist, or a combination of the above.

\* \* \* \* \*